United States Patent [19]
Vannice et al.

[11] 4,171,320
[45] Oct. 16, 1979

[54] HYDROCARBON SYNTHESIS FROM CO AND $H_2$ USING RU SUPPORTED ON GROUP VB METAL OXIDES

[75] Inventors: M. Albert Vannice, Boalsburg, Pa.; Samuel J. Tauster, Englishtown, N.J.

[73] Assignee: Exxon Research & Engineering Co., Florham Park, N.J.

[21] Appl. No.: 843,497

[22] Filed: Oct. 19, 1977

[51] Int. Cl.$^2$ .............................................. C07C 1/04
[52] U.S. Cl. .................... 260/449 R; 252/432; 252/444; 252/435 R; 252/456; 252/458; 252/460; 252/464; 252/465; 252/466 PT
[58] Field of Search .................................. 260/449 R

[56] References Cited

U.S. PATENT DOCUMENTS

| | | | |
|---|---|---|---|
| 2,553,398 | 5/1951 | Atwell | 260/449 R |
| 2,583,611 | 1/1952 | Sullivan | 260/449 R |
| 2,616,914 | 11/1952 | Riblett | 260/449 R |
| 4,042,614 | 8/1977 | Vannice et al. | 260/449 R |

OTHER PUBLICATIONS

Shultz et al., Bureau of Mines Report of Investigations, No. 6974, (1967) Noble Metals, Molybdenum & Tungsten in Hyd Synthesis.

*Primary Examiner*—Howard T. Mars
*Attorney, Agent, or Firm*—E. A. Forzano; J. J. Allocca

[57] ABSTRACT

An improved method for the synthesis of hydrocarbons with reduced methane formation and for the selective generation of olefinic hydrocarbons, preferably $C_2$–$C_5$ olefins inclusive, which method comprises the steps of passing a CO and $H_2$ synthesis gas stream over a catalyst at a temperature and pressure for a time sufficient to generate the desired olefinic products, wherein the improvement consists in using as a catalyst ruthenium on a support comprising at least one refractory Group VB metal oxide. The weight loading of the ruthenium may range from about 0.01 to about 15 wt. % based on the total catalyst weight. The ruthenium average crystallite size is preferably less than 5 nm (50Å). The operating conditions of the instant process are typical for Fischer-Tropsch synthesis.

17 Claims, No Drawings

HYDROCARBON SYNTHESIS FROM CO AND $H_2$ USING RU SUPPORTED ON GROUP VB METAL OXIDES

FIELD OF THE INVENTION

Brief Description of the Invention

An improved method for the synthesis of hydrocarbons with reduced methane formation and for the selective generation of olefinic hydrocarbons, preferably $C_2-C_5$ olefins inclusive, which method comprises the steps of passing a CO and $H_2$ synthesis gas stream over a catalyst at a temperature and pressure for a time sufficient to generate the desired olefinic products wherein the improvement consists in using as a catalyst ruthenium on a support comprising at least one refractory Group VB metal oxide. The weight loading of the ruthenium may range from about 0.01 to about 15 wt.% based on the weight of the total catalyst. The ruthenium average crystallite size is preferably less than 5 nm (50 Å). The operating conditions of the instant process are typical for Fischer-Tropsch synthesis.

DETAILED DESCRIPTION OF THE INVENTION

An improved method for the synthesis of hydrocarbons with reduced methane formation and for the selective generation of olefinic hydrocarbons, preferably $C_2-C_5$ olefins inclusive, which method comprises the steps of passing a CO and $H_2$ synthesis gas stream over a catalyst at a temperature and pressure for a time sufficient to generate the desired olefinic products wherein the improvement consists in using as a catalyst ruthenium on a support comprising at least one refractory Group VB metal oxide.

The instant invention presents an improvement in the Fischer-Tropsch hydrocarbon synthesis method in that it has been discovered unexpectedly that a ruthenium catalyst supported on a refractory Group VB metal oxide, or mixtures thereof, when utilized in conjunction with the Fischer-Tropsch method, will generate, with greater selectivity, olefinic hydrocarbons with reduced production of methane and other paraffinic products.

The instant process exhibits this selectivity to olefinic products, preferably $C_2-C_5$ olefins inclusive, when the catalyst utilized comprises ruthenium supported on a supported selected from the group consisting of a refractory Group VB metal oxide, or mixtures thereof, preferably $V_2O_3$, $Nb_2O_5$ and $Ta_2O_5$. The support may also be selected from the group consisting of $V_2O_3$, $Nb_2O_5$, $Ta_2O_5$, $Al_2O_3-V_2O_3$, $Al_2O_3-Nb_2O_5$, $Al_2O_3-Ta_2O_5$, $SiO_2-V_2O_3$, $SiO_2-Ta_2O_5$, $SiO_2-Nb_2O_5$, $V_2O_3$-carbon, $Nb_2O_5$-carbon, $Ta_2O_5$-carbon, alkaline earth-Group VB oxides, alkali-Group VB oxides, rare earth Group VB oxides, Group IVB-Group VB oxides, or mixtures thereof, but is preferably oxides of vanadium, oxides of tantalum and oxides of niobium or mixtures thereof or admixed with alumina, silica or Group IVB oxides. Most preferably, the support comprises essentially pure $V_2O_3$, $Nb_2O_5$ or $Ta_2O_5$ or mixtures thereof either alone or in combination with alumina, silica or Group IVB oxides. It is also possible to admix with these materials other refractory materials that will not substantially inhibit the Fischer-Tropsch hydrocarbon synthesis characteristics of ruthenium supported on at least one Group VB metal oxide as herein described. The supports which may be used in the practice of this invention may be in any form, such as powders, pellets, spheres, extrudates, etc. and may have a B.E.T. surface area of from about 1 to about 200 $m^2g^{-1}$, preferably from about 10 to about 100 $m^2g^{-1}$, most preferably from 25 to about 100 $m^2g^{-1}$. With most metal catalysts, the higher the surface area of the support, the higher the dispersion of the supported metal at a given weight loading. It is therefore desirable to use a support with as high a surface area as possible to maximize the dispersion of the ruthenium metal. Ruthenium is deposited on the chosen support in a concentration of from about 0.01 to about 15 wt.%, preferably from about 0.1 to about 10 wt.%, and most preferably from about 0.5 to about 5 wt.%, the percentages based on total weight of catalyst with the ruthenium possessing an average crystallite size, as determined by standard techniques such as X-ray diffraction of from about 1 to about 20 nm, preferably about 1 to about 10 nm, and most preferably from about 1 to about 5 nm. Using standard experimental techniques, for a ruthenium on $Nb_2O_5(650)$, $Ta_2O_5(650)$ or $V_2O_3(650)$ system, reduced in hydrogen at 450° C., X-ray diffraction shows no particles of Ru in the reduced catalyst, indicating particles of Ru having crystallite sizes of less than 5 nm, which corresponds to a dispersion of greater than 20%.

Ruthenium catalysts comprising ruthenium supported on a support comprising a refractory Group VB metal oxide, or mixtures thereof, exhibit greater selectivity to the production of olefinic products with decreased methane formation as compared with typical ruthenium catalysts of the prior art. The prior art catalysts are either unsupported or supported on such materials as $Al_2O_3$, $SiO_2$ or carbon.

The operating conditions of the instant process are typical for Fischer-Tropsch synthesis. The pressure may range from about 100 to about $10^5$ kPa, preferably from about 100 to about 3100 kPa, and most preferably from about 100 to about 2060 kPa. The temperature may range from about 100° to about 500° C., preferably from about 150° to about 400° C., and most preferably from about 150° to about 300° C. The $H_2$/CO ratio may range from about 0.1 to about 10, preferably from about 0.5 to about 4, most preferably from about 1 to about 3. The space velocity may range from about 100 $hr^{-1}$ to about 50,000 $hr^{-1}$.

The ruthenium catalysts employed in the practice of the instant process are themselves prepared by techniques known in the art for the preparation of other catalyst systems, such as Ru on $Al_2O_3$, etc. A suitable ruthenium salt, such as ruthenium chloride, ruthenium nitrate or ruthenium acetate, etc., is dissolved in a solvent such as water or any other suitable solvent and stirred with the chosen Group VB metal oxide support system. After thorough mixing the mixture is allowed to dry and then heat treated in air at a temperature of from 100° to 150° C. or alternatively may be dried immediately by heating in air at a temperature of between 100° and 150° C. for several hours.

In a preferred embodiment, the ruthenium catalyst, prepared as outlined above, or by similar techniques, is heat treated in a reducing atmosphere such as hydrogen at a temperature greater than 300° C., preferably greater than 400° C., most preferably greater than 500° C., for from typically 0.5 to 4 hours, preferably from 1–2 hours. U.S. Ser. No. 771,396, filed Feb. 23, 1977, copending application of S. J. Tauster, L. L. Murrell and S. C. Fung, teaches the procedures of preparing catalysts by this method and is hereby incorporated by reference. It should be noted that this heat treating reduction step need not be practiced as a separate step, since the Fischer-Tropsch synthesis is practiced in a reducing atmosphere and will, therefore, have a similar reduction effect on the catalyst as the above step. The supported ruthenium catalyst system utilized in the instant process may have an average ruthenium crystallite size of preferably less than 5 nm.

The following examples are presented to illustrate and not limit the instant invention.

EXAMPLE 1

The selectivity in a Fischer-Tropsch synthesis for ruthenium catalysts supported by $Nb_2O_5$ is compared to ruthenium catalysts both unsupported and supported by support materials of the prior art.

A 1% $Ru/Nb_2O_5$ catalyst was prepared in the following manner. $Nb_2O_5$ was prepared by the addition of a methanolic solution of $NbCl_5$ to a methanolic solution of $NH_4OH$, producing a gel. The latter was washed with $H_2O$, then with 0.2 M $NH_4NO_3$, followed by another wash with $H_2O$. This gel was dried at 110° C. The dried gel was calcined in air at 600° C. for 16 hours. X-ray inspection of the calcined product indicated the presence of $Nb_2O_5$ with no other phases apparent. The surface area (B.E.T.) was 7.9 m²/g. A portion of $Nb_2O_5$ was treated in flowing $H_2$ (20% in He) at 650° C. for 1½ hours. The product was labeled $Nb_2O_5(650)$. X-ray inspection showed the presence of $Nb_2O_5$ and of $NbO_2$, the latter being in a lesser amount.

The $Nb_2O_5$ and $Nb_2O_5(650)$ prepared in the above manner were impregnated by the method of incipient wetness with aqueous solutions of $RuCl_3$. The impregnates were dried at 110° C. The amount of $RuCl_3$ used was calculated to provide 1% Ru by total weight of catalyst after reduction in $H_2$. The $RuCl_3/Nb_2O_5$ was charged after drying into the catalytic reactor for in situ reduction in $H_2$.

The $RuCl_3/Nb_2O_5(650)$ was treated in flowing $H_2$ (20% in He) at 650° C., for 1½ hours, then cooled in flowing He and passivated by treatment with flowing, dilute $O_2$ (1% in He) at 25° C. This material was thereupon charged into the catalytic reactor where it underwent in situ reduction in $H_2$.

The ruthenium metal catalyst was prepared as follows. $NH_4OH$ was added to an aqueous solution of $RuCl_3$ precipitating $Ru(OH)_3$ which was subsequently dried at 110°–120° C. in air. It was then charged to the reactor and flushed with He at room temperature. The $H_2$ concentration in the He stream was slowly increased at a rate such that the sample did not heat up excessively. When 100% $H_2$ was flowing over the sample, the temperature was increased to 300° C. over a period of 1 hour and held at 300° C. for 1 hour. Subsequently it was cooled to reaction temperature in $H_2$ for catalytic studies. The ruthenium catalysts supported on carbon, $SiO_2$ and $\eta\text{-}Al_2O_3$ were made in a manner similar to the $Ru/Nb_2O_5$: the ruthenium was deposited on the supports by the incipient wetness technique using $RuCl_3$; they were dried at 110°–120° C. in air; and reduced in situ. The carbon for the ruthenium on carbon catalyst was Carbolac-1, obtained from the Cabot Corporation, had a B.E.T. surface area of 950 m²g⁻¹. The $SiO_2$ for the ruthenium on $SiO_2$ catalyst was Cab-O-Sil (HS-5), obtained from the Cabot Corporation, had a B.E.T. surface area of 300 m²g⁻¹. The $Al_2O_3$ for the ruthenium on $\eta\text{-}Al_2O_3$ was prepared by calcining alumina B-trihydrate ($Al_2O_3 \cdot 3H_2O$), obtained from Davison Chemical Co., at 600° C. in air for 4 hours. It had a B.E.T. surface area of 245 m²g⁻¹.

TABLE I

SELECTIVITY OF VARIOUS RUTHENIUM CATALYSTS
(Reaction Conditions: $H_2/CO$ = 3; Pressure = 103 kPa)

| Catalyst | T°C. | % CO Conv | Hydrocarbon Product Distribution (Mole %) | | | | | | | | |
|---|---|---|---|---|---|---|---|---|---|---|---|
| | | | $CH_4$ | $C_2H_4$ | $C_2H_6$ | $C_3H_6$ $C_3H_8$ | $C_4H_8$ $C_4H_{10}$ | $C_5H_{10}$ $C_5H_{12}$ | $C_6^+$ | $C_2$–$C_5$ Olefins | $C_2^+$ |
| Ru metal[c] | 226 | 3.5 | 96 | 0 | 4 | TR. | 0 | 0 | 0 | 0 | 4 |
| 4% Ru/Carbon[b] | 243 | 2.5 | 98 | 0 | 2 | TR. | 0 | 0 | 0 | 0 | 2 |
| | 234 | 1.6 | 98 | 0 | 2 | 0 | 0 | 0 | 0 | 0 | 2 |
| 1% Ru/SiO₂[a] | 232 | 4.1 | 87 | ½ | 7 | 4 | 1 | 1 | TR. | 2½ | 13 |
| 5% Ru/SiO₂[a] | 233 | 16.7 | 86 | TR. | 8 | 4 | 1½ | 1 | TR. | TR. | 14 |
| 1% Ru/Al₂O₃[a] | 228 | 8.8 | 66 | ----12---- | | 8½ | 6 | 4½ | 3 | 11 | 34 |
| | 244 | 14.1 | 71 | ----11---- | | 7 | 5 | 4 | 2 | 10 | 29 |
| Ru/Al₂O₃[a] | 239 | 13.6 | 67 | ½ | 10 | 10 | 10 | 6 | 5 | — | 33 |
| 1% Ru/Nb₂O₅[a] | 234 | 7.8 | 48 | ----11---- | | 13 | 10 | 7 | 12 | 22 | 52 |
| 1% Ru/Nb₂O₅(650)[a] | 244 | 5.7 | 41 | ----14---- | | 18 | 11 | 11 | 5 | 27 | 59 |

[a]Catalysts reduced for 1 hour at 450° C. before feed introduced.
[b]Catalyst reduced for 1 hour at 400° C. before feed introduced.
[c]Catalyst reduced for 1 hour at 300° C. before feed introduced.

Table I illustrates in a Fischer-Tropsch synthesis the desirable selectivity characteristics of $Ru/Nb_2O_5$ catalysts as compared with unsupported Ru metal or with catalysts consisting of ruthenium supported on other support materials. In particular, it should be noted that the formation of methane is significantly lower for the $Ru/Nb_2O_5$ catalysts than for the other catalysts listed. Thus, whereas the selectivity in the production of $C_2+$ is up to 34 mole % for all the other catalysts listed in Table I, values up to 59 moles % are obtained for a Ru catalyst supported on $Nb_2O_5$. A further desirable feature of the $Ru/Nb_2O_5$ catalyst is its enhanced formation of $C_2$–$C_5$ olefins. These olefins are useful chemical intermediates for the production of plastics, rubber, alcohols, ketones, aldehydes, esters and acids. It is shown in Table I that the $Ru/Nb_2O_5$ catalysts exhibit at least twice the selectivity in the production of $C_2$–$C_5$ olefins as any other catalyst listed.

EXAMPLE 2

The selectivity in a Fischer-Tropsch synthesis for ruthenium catalysts supported by $Ta_2O_5$ is compared to ruthenium catalysts both unsupported and supported by support materials of the prior art.

A 1% $Ru/Ta_2O_5$ catalyst was prepared in the following manner. $Ta_2O_5$ was prepared by the addition of a methanolic solution of $TaCl_5$ to a methanolic solution of $NH_4OH$, producing a gel. The latter was washed with $H_2O$, then with 0.2 M $NH_4NO_3$, followed by another wash with $H_2O$. This gel was dried at 110° C. The dried gel was calcined in air at 600° C. for 4 hours. X-ray inspection of the calcined product indicated the presence of $Ta_2O_5$ with no other phases apparent. The material was recalcined in air at 700° C. for 16 hours. The surface area (B.E.T.) was 5.3 m²/g.

A portion of the $Ta_2O_5$ was treated with flowing $H_2$ (20% in He) at 650° C. for 1½ hours. The product was labeled $Ta_2O_5(650)$. X-ray inspection again showed $Ta_2O_5$ with no other phases apparent.

$Ta_2O_5$ and $Ta_2O_5(650)$ were impregnated by the method of incipient wetness with aqueous solutions of $RuCl_3$. The amount of $RuCl_3$ was calculated to provide 1% Ru by weight after reduction in $H_2$. $RuCl_3/Ta_2O_5$ was charged, after drying, into the catalytic reactor for in situ reduction in $H_2$.

$RuCl_3/Ta_2O_5(650)$ was treated in flowing $H_2$ (20% in He) at 650° C., for 1½ hours, then cooled in flowing He and passivated by treatment with flowing, dilute $O_2$ (1% in He) 25° C. This material was thereupon charged into the catalytic reactor wherein it underwent in situ activation in $H_2$. The other catalysts were prepared as described in Example 1.

Table II illustrates in a Fischer-Tropsch synthesis the desirable selectivity characteristics of $Ru/Ta_2O_5$ catalysts as compared with unsupported Ru metal or with catalysts consisting of ruthenium supported on other support materials. The other catalysts were prepared as described in Example 1. The data pertaining to Ru metal, Ru/carbon, $Ru/SiO_2$ and $Ru/Al_2O_3$ are identical to that presented in Table I and are repeated for convenience. It is seen that the desirable selectivity characteristics which were pointed out with respect to $Ru/Nb_2O_5$ catalysts in Table I also apply to $Ru/Ta_2O_5$ catalysts. Thus, the molar selectivities of the $Ru/Ta_2O_5$ catalyst in the production of $C_2+$ hydrocarbons are in excess of 50%—considerably greater than the molar selectivity to the $C_2+$ hydrocarbons of the prior art catalysts listed. Table II also indicates that the $Ru/Ta_2O_5$ catalysts exhibit markedly enhanced selectivity in the production of $C_2-C_5$ olefins as compared to any other catalyst listed.

A 1% $Ru/V_2O_3$ catalyst was prepared in the following manner:

$V_2O_3$ was made as follows: $NH_4VO_3$ was calcined at about 400° C. in flowing air to give $V_2O_5$. The surface area (B.E.T.) was 11 m²/g. The $V_2O_5$ was reduced in flowing $H_2$ (20% in He) at 550° C. for 2½ hours. X-ray inspection showed $V_2O_3$ with a small extraneous signal at 20°=27°. The latter indicates the presence to a very small extent, of a crystallographic shear phase of the family, $V_mO_{2m-1}$. The surface area (B.E.T.) was 2.4 m²/g.

A portion of $V_2O_3$ was treated in flowing $H_2$ (20% in He) at 650° C. for 1½ hours. The product was labelled $V_2O_3(650)$. X-ray inspection indicated the presence of $V_2O_3$ with no other phases apparent. Thus, the very small amount of higher vanadium oxide present before $H_2$ treatment at 650° C. had been removed by this treatment.

$V_2O_3$ and $V_2O_3(650)$ were impregnated by the method of incipient wetness with aqueous solutions of $RuCl_3$. The impregnates were dried at 110° C. The amount of $RuCl_3$ used was calculated to provide 1% Ru by weight after reduction in $H_2$. $RuCl_3/V_2O_3$ was charged, after drying, into the catalytic reactor for in situ reduction in $H_2$.

$RuCl_3/V_2O_3(650)$ was treated in flowing $H_2$ (20% in He) at 650° C., 1½ hours, then cooled in flowing He and passivated by treatment with flowing, dilute $O_2$ (1% in He) at 25° C. This material was thereupon charged into the catalytic reactor where it underwent in situ activation in $H_2$.

Table III illustrates in a Fischer-Tropsch synthesis the desirable selectivity characteristics of $Ru/V_2O_3$ catalysts as compared with unsupported Ru metal or with catalysts consisting of ruthenium supported on other support materials. The data pertaining to Ru metal, Ru/Carbon, $Ru/SiO_2$ and $Ru/Al_2O_3$ are identical to that presented in Tables I and II and are repeated in Table III for convenience. It is seen that the desirable selectivity characteristics which were demonstrated with respect to $Ru/Nb_2O_5$ catalysts in Table I and $Ru/Ta_2O_5$ catalysts in Table II also apply to $Ru/V_2O_3$ cata-

TABLE II

SELECTIVITY OF VARIOUS RUTHENIUM CATALYSTS
(Reaction Conditions: $H_2/CO$ = 3; Pressure = 103 kPa)

| Catalyst | T °C. | % CO Conv | Hydrocarbon Product Distribution (Mole %) | | | | | | | | | |
|---|---|---|---|---|---|---|---|---|---|---|---|---|
| | | | $CH_4$ | $C_2H_4$ | $C_2H_6$ | $C_3H_6$ $C_3H_8$ | $C_4H_8$ $C_4H_{10}$ | $C_5H_{10}$ $C_5H_{12}$ | $C_6+$ | $C_2-C_5$ Olefins | $C_2+$ |
| Ru metal[c] | 226 | 3.5 | 96 | 0 | 4 | TR. | 0 | 0 | 0 | 0 | 4 |
| 4% Ru/Carbon[b] | 243 | 2.5 | 98 | 0 | 2 | TR. | 0 | 0 | 0 | 0 | 2 |
| | 234 | 1.6 | 98 | 0 | 2 | 0 | 0 | 0 | 0 | 0 | 2 |
| 1% $Ru/SiO_2$[a] | 232 | 4.1 | 87 | ½ | 7 | 4 | 1 | 1 | TR. | 2½ | 13 |
| 5% $Ru/SiO_2$[a] | 233 | 16.7 | 86 | TR. | 8 | 4 | 1½ | 1 | TR. | TR. | 14 |
| 1% $Ru/Al_2O_3$[a] | 228 | 8.8 | 66 | ----12---- | | 8½ | 6 | 4½ | 3 | 11 | 34 |
| | 244 | 14.1 | 71 | ----11---- | | 7 | 5 | 4 | 2 | 10 | 29 |
| 5% $Ru/Al_2O_3$[a] | 239 | 13.6 | 67 | ½ | 10 | 10 | 10 | 6 | 5 | — | 33 |
| 1% $Ru/Ta_2O_5$[a] | 228 | 17.7 | 46 | ----10---- | | 13 | 10 | 11 | 9 | 17 | 54 |
| 1% $Ru/Ta_2O_5(650)$[a] | 226 | 10.3 | 42 | ----10---- | | 16 | 12 | 9 | 11 | 27 | 58 |

[a]Catalysts reduced for 1 hour at 450° C. before feed introduced.
[b]Catalyst reduced for 1 hour at 400° C. before feed introduced.
[c]Catalyst reduced for 1 hour at 300° C. before feed introduced.

EXAMPLE 3

The selectivity in a Fischer-Tropsch synthesis for ruthenium catalysts supported by $V_2O_3$ is compared to ruthenium catalysts both unsupported and supported by other support materials of the prior art.

lysts. Thus, the molar selectivities of the $Ru/V_2O_3$ catalysts in the production of $C_2+$ are about 50%—considerably greater than the molar selectivity to the $C_2+$ hydrocarbons of the other catalysts listed. Formation of $C_2-C_5$ olefins is also markedly enhanced for $Ru/V_2O_3$. In the case of $Ru/V_2O_3(650)$, formation of propylene, butene and pentene was not measured. However, the high selectivity with which ethylene is formed by this catalyst (17% or 16%, as compared with ½% over 5% Ru/Al$_2$O$_3$) is significant.

TABLE III

SELECTIVITY OF VARIOUS RUTHENIUM CATALYSTS
(Reaction Conditions: H$_2$/CO = 3, Pressure = 103 kPa)

| Catalyst | T °C. | % CO Conv | Hydrocarbon Product Distribution (Mole %) | | | | | | | | |
|---|---|---|---|---|---|---|---|---|---|---|---|
| | | | CH$_4$ | C$_2$H$_4$ | C$_2$H$_6$ | C$_3$H$_6$ C$_3$H$_8$ | C$_4$H$_8$ C$_4$H$_{10}$ | C$_5$H$_{10}$ C$_5$H$_{12}$ | C$_6$+ | C$_2$–C$_5$ Olefins | C$_2$+ |
| Ru metal$^c$ | 226 | 3.5 | 96 | 0 | 4 | TR. | 0 | 0 | 0 | 0 | 4 |
| 4% Ru/Carbon$^b$ | 243 | 2.5 | 98 | 0 | 2 | TR. | 0 | 0 | 0 | 0 | 2 |
| | 234 | 1.6 | 98 | 0 | 2 | 0 | 0 | 0 | 0 | 0 | 2 |
| 1% Ru/SiO$_2$$^a$ | 232 | 4.1 | 87 | ½ | 7 | 4 | 1 | 1 | TR. | 2½ | 13 |
| 5% Ru/SiO$_2$$^a$ | 233 | 16.7 | 86 | TR. | 8 | 4 | 1½ | 1 | TR. | TR. | 14 |
| 1% Ru/Al$_2$O$_3$$^a$ | 228 | 8.8 | 66 | ----12---- | | 8½ | 6 | 4½ | 3 | 11 | 34 |
| | 244 | 14.1 | 71 | ----11---- | | 7 | 5 | 4 | 2 | 10 | 29 |
| 5% Ru/Al$_2$O$_3$$^a$ | 239 | 13.6 | 67 | ½ | 10 | 10 | 10 | 6 | 5 | — | 33 |
| 1% Ru/V$_2$O$_3$$^a$ | 243 | 4.1 | 45 | 6 | 9 | 18 | 10 | 3 | 10 | 28 | 55 |
| 1% Ru/V$_2$O$_3$(650)$^a$ | 246 | 0.7 | 55 | 17 | 4 | 17 | 6 | — | — | — | 45 |
| | 259 | 1.4 | 49 | 16 | 5 | 17 | 6 | 8 | — | — | 51 |

$^a$Catalysts reduced for 1 hour at 450° C. before feed introduced
$^b$Catalyst reduced for 1 hour at 400° C. before feed introduced
$^c$Catalyst reduced for 1 hour at 300° C. before feed introduced

What is claimed is:

1. A process for the synthesis of olefins of from C$_2$ to C$_5$ chain length inclusive, said process comprising the steps of passing H$_2$ and CO at a H$_2$/CO ratio of 0.1 to about 10 over a catalyst comprising ruthenium on a support selected from the group consisting of V$_2$O$_3$, Nb$_2$O$_5$, Ta$_2$O$_5$, Al$_2$O$_3$-V$_2$O$_3$, Al$_2$O$_3$-Nb$_2$O$_5$, Al$_2$O$_3$-Ta$_2$O$_5$, SiO$_2$-V$_2$O$_3$, SiO$_2$-Nb$_2$O$_5$, SiO$_2$-Ta$_2$O$_5$, V$_2$O$_3$-carbon, Nb$_2$O$_5$-carbon, Ta$_2$O$_5$-carbon, alkaline earth-group VB oxides, alkali-Group VB oxides, rare earth-Group VB oxides, Group IVB-Group VB oxides and mixtures thereof, at a space velocity of from 100 to 50,000 hr$^{-1}$, at a temperature of from 100° to 500° C., at a pressure of from 100 to 10$^5$ kPa for a time sufficient to effect the generation of the desired olefinic products wherein the concentration of said ruthenium in said catalyst is from 0.01 to 15 wt. % based on total catalyst weight.

2. The process of claim 1 wherein the support comprising a Group VB metal oxide or mixture thereof is selected from the group consisting of V$_2$O$_3$, Nb$_2$O$_5$, Ta$_2$O$_5$, Al$_2$O$_3$-V$_2$O$_3$, Al$_2$O$_3$-Nb$_2$O$_5$, Al$_2$O$_3$-Ta$_2$O$_5$, SiO$_2$-V$_2$O$_3$, SiO$_2$-Nb$_2$O$_5$, SiO$_2$-Ta$_2$O$_5$, V$_2$O$_3$-carbon, Nb$_2$O$_5$-carbon, Ta$_2$O$_5$-carbon, alkaline earth-Group VB oxides, alkali-Group VB oxides, rare earth-Group VB oxides, Group IVB-Group VB oxides and mixtures thereof.

3. The process of claim 1 wherein the Group VB metal oxide is selected from the group consisting of V$_2$O$_3$, Nb$_2$O$_5$, Ta$_2$O$_5$, and mixtures thereof.

4. The process of claim 1 wherein the Group VB metal oxide is V$_2$O$_3$.

5. The process of claim 1 wherein the group VB metal oxide is Nb$_2$O$_5$.

6. The process of claim 1 wherein the group VB metal oxide is Ta$_2$O$_5$.

7. The process of claim 1 wherein the ruthenium concentration is from about 0.1 to about 10 wt. % based on the total weight of the catalyst.

8. The process of claim 7 wherein the ruthenium concentration is from about 0.5 to about 5 wt. % based on the total weight of the catalyst.

9. The process of claim 2 wherein said ruthenium supported catalyst has a ruthenium particle crystallite size of from about 1 to about 20 nm.

10. The process of claim 9 wherein said ruthenium particle crystallite size is from about 1 to about 10 nm.

11. The process of claim 10 wherein said ruthenium particle crystallite size is from about 1 to about 5 nm.

12. The process of claim 1 wherein the catalyst is reduced at a temperature of greater than 300° C.

13. The process of claim 1 wherein the support has a surface area of from about 1 to about 200 m$^2$g$^{-1}$.

14. The process of claim 1 wherein the H$_2$/CO ratio is about 0.5 to about 4, the pressure is from about 100 to 3100 kPa and the temperature is about 150° to about 400° C.

15. The process of claim 1 wherein the H$_2$/CO ratio is about 1 to about 3, the pressure is from about 100 to about 2060 kPa and the temperature is about 150° to about 300° C.

16. The process of claim 14 wherein the support is Nb$_2$O$_5$.

17. The process of claim 14 wherein the support is Ta$_2$O$_5$.

* * * * *